(12) United States Patent
Ishida et al.

(10) Patent No.: US 6,530,886 B1
(45) Date of Patent: Mar. 11, 2003

(54) METHOD AND APPARATUS FOR MEASURING SUBCUTANEOUS FAT USING ULTRASONIC WAVE

(75) Inventors: Hideaki Ishida, Akita (JP); Eiichi Serita, Akita (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/678,795

(22) Filed: Oct. 4, 2000

(30) Foreign Application Priority Data

Oct. 8, 1999 (JP) ............................................. 11-287601
Oct. 8, 1999 (JP) ............................................. 11-287602

(51) Int. Cl.[7] ................................................. A61B 8/00
(52) U.S. Cl. ....................... 600/442; 600/437; 600/443; 600/447; 600/449
(58) Field of Search ................................. 600/437, 442, 600/449, 443

(56) References Cited

FOREIGN PATENT DOCUMENTS

| JP | 11-113870 | | 4/1999 |
|---|---|---|---|
| JP | 02000350727 A | * | 12/2000 |
| NL | 001213099-2305 | | 1/2001 |
| WO | WO 98/17178 | | 4/1998 |
| WO | WO 99/65395 | | 12/1999 |

OTHER PUBLICATIONS

PCT/US99/13515. Lang et al. Jun. 15, 1998.*

* cited by examiner

Primary Examiner—Marvin M. Lateef
Assistant Examiner—Ruby Jain
(74) Attorney, Agent, or Firm—McDermott, Will & Emery

(57) ABSTRACT

Disclosed is a method for measuring subcutaneous fat using an ultrasonic wave, comprising a step of measuring a portion of an abdomen on a median line of a person under test. The present invention also provides an apparatus for measuring subcutaneous fat using an ultrasonic wave. The apparatus comprises: a reference position setting device which sets said apparatus at a reference position for measurement on a person under test; an ultrasonic transmitter disposed at the predetermined position relative to said reference position setting device; and an ultrasonic receiver disposed at the predetermined position relative to said reference position setting device. According to the present invention, a navel of the person is defined as the reference position for measurement. The area to be measured on the abdomen of the person is located along the median line between the sternum and the pubis of the person. Furthermore, the ultrasonic transmitter and the ultrasonic receiver are disposed for measuring the subcutaneous fat in a position around 2 cm above the navel of the person along a median line.

22 Claims, 6 Drawing Sheets

ABDOMEN OF
PERSON UNDER TEST ←

METHOD AND APPARATUS FOR MEASURING SUBCUTANEOUS FAT USING ULTRASONIC WAVE

BACKGROUND OF THE INVENTION

1. Field of the Invention

The present invention relates to a method and an apparatus for measuring subcutaneous fat using an ultrasonic wave.

2. Description of the Prior Art

In the past, the measurement of thickness of subcutaneous fat using an ultrasonic wave has been conducted only by physicians, practitioners and other skilled persons, based upon their experiences and according to manuals for measuring apparatus. And the measurement was generally performed at arbitrary selected parts or positions on a person under test, including those at the side of the navel, on the flank, on the back face of an upper arm and the like.

In such prior art measuring process, an assistant person becomes necessary for performing the measurement, in addition to a person under test, depending on what part of the person is to be measured. Further, it is difficult to properly select the part to be measured among the many parts of the person as described above. It follows that the part to be measured may vary depending on what kind of person conducts the measurement, and the repeatability of the measurement results becomes lower. In addition, the measurement of subcutaneous fat at those parts is to measure the reflected wave from an interface between the fat layer and the muscle layer. Therefore, the prior art measuring process is defective in that the measurement result is greatly affected by condition of the muscle.

The present invention is directed to solve the problems of the prior art by providing new and improved measuring method and apparatus that enable the measurement always at the same parts or positions and can produce reliable results of measurement with higher repeatability.

SUMMARY OF THE INVENTION

In view of the above, the present invention provides a method for measuring subcutaneous fat using an ultrasonic wave, characterized in that it comprises the step of:

measuring a portion of an abdomen on a median line of a person under test.

In this respect, preferably, the portion of the abdomen on the median line is between a sternum and a pubis of the person under test. The portion of the abdomen on the median line is around 2 cm above a navel of the person under test.

According to another aspect, the present invention provides an apparatus for measuring subcutaneous fat using an ultrasonic wave, characterized in that it comprises:

a reference position setting device which sets said apparatus at a reference position for measurement on a person under test;

an ultrasonic transmitter disposed at the predetermined position relative to said reference position setting device; and an ultrasonic receiver disposed at the predetermined position relative to said reference position setting device.

In this respect, preferably, a navel of the person is defined as the reference position for measurement. The ultrasonic transmitter and the ultrasonic receiver are disposed for measuring the subcutaneous fat in an area around 2 cm above the navel of the person along a median line. A shoulder joint of the person is defined as the reference position for measurement. The ultrasonic transmitter and the ultrasonic receiver are formed by one and the same device. The apparatus further comprises a measurement start switch, which measurement start switch is provided on the upper side of the apparatus.

This invention will now be described in further detail with regard to preferred embodiments as illustrated in the accompanying drawings.

Figure 1:
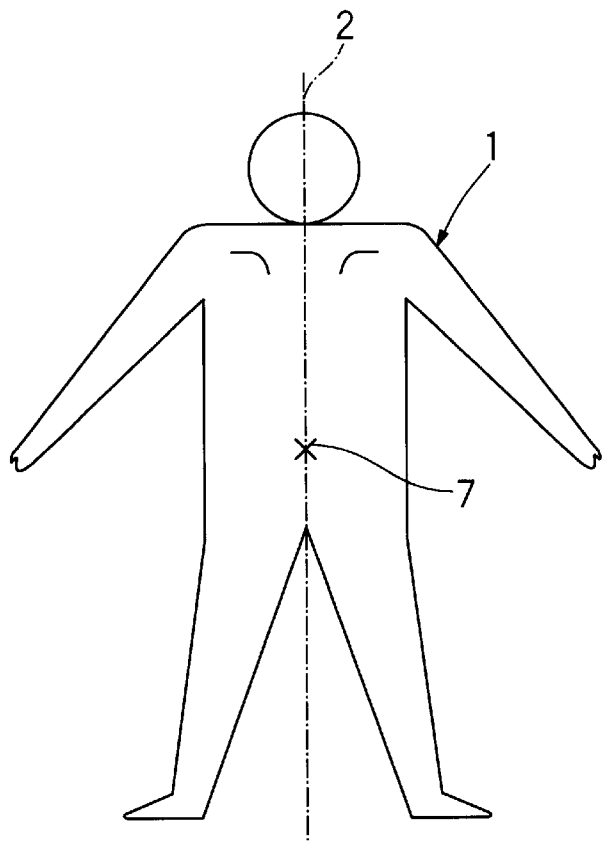
FIG. 1 is a view representing a measuring point on a person under test for measuring the thickness of subcutaneous fat.
Figure 2:
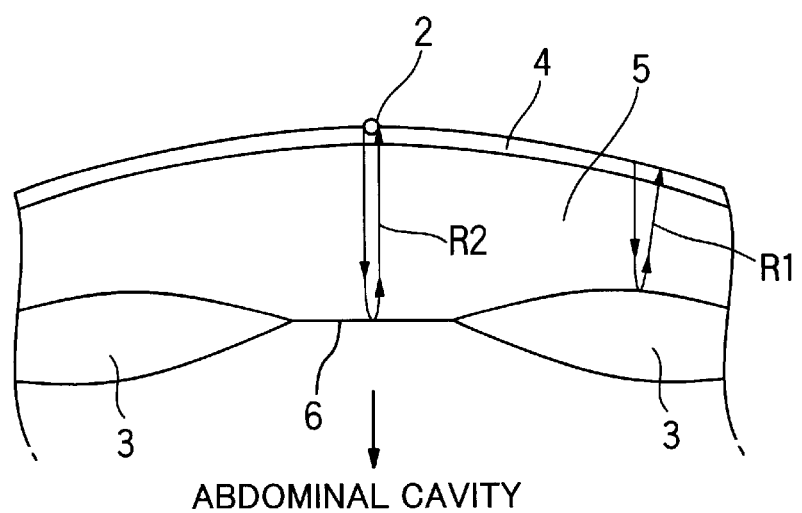
FIG. 2 is a cross section view representing an abdomen of the person.

DESCRIPTION OF THE PRIFERRED EMBODIMENTS:

Referring first to FIG. 1 that shows a measuring position on a person under test 1, an ultrasonic measurement for measuring subcutaneous fat for the person is performed in his abdominal region along a median line or a center line 2 of the person. Referring to FIG. 2 that is a cross section view of an abdomen of the person, an area of the abdomen on the median line 2 can be considered as a region(linea alba) in which right and left rectus abdominis muscles 3 are coupled together by means of a coupling tissue. Such region of the abdomen is rarely subject to the influence of the rectus abdominis muscles 3 upon performing the ultrasonic measurement. If the ultrasonic wavers generated over a skin 4 at the position away from the median line 2, the reflected ultrasonic wave can not reliably be received, as shown by "R1" in FIG. 2, and as the result, significant error may be produced. The reason for it is that there may be some variations present between individuals in an angle of an interface between the subcutaneous fat 5 and the muscles 3 as well as some variations in condition of such interface under the tension of the muscles 3 due to respiration, etc. However, when the measurement is performed in an area along the median line 2, there is no such influence of the muscles 3 produced. Then the reliable measurement for the thickness of subcutaneous fat 5 can be achieved with the reflected wave "R2" from a portion indicated by a linea alba 6.

The measuring area along the median line 2 on the abdomen of the person is defined as a no-bone area ranging from the sternum to the pubis. In this connection, an area around the navel should be excluded because of the adverse effect of the navel itself. Especially, the measuring area around 2 cm above the navel for measuring the thickness of subcutaneous fat can produce good correlation between the area of abdominal subcutaneous fat and the total amount of subcutaneous fat, as measured by CT scan, etc. Therefore, the area of abdominal subcutaneous fat and the total amount of subcutaneous fat can easily be estimated from the measured thickness of subcutaneous fat.

When performing the measurement along the median line 2, it is preferable that the position of the navel 7 on the median line 2 is used as the reference point, because of no possibility of positional deviation produced and of easy measurement achieved by every body.

Figure 3:
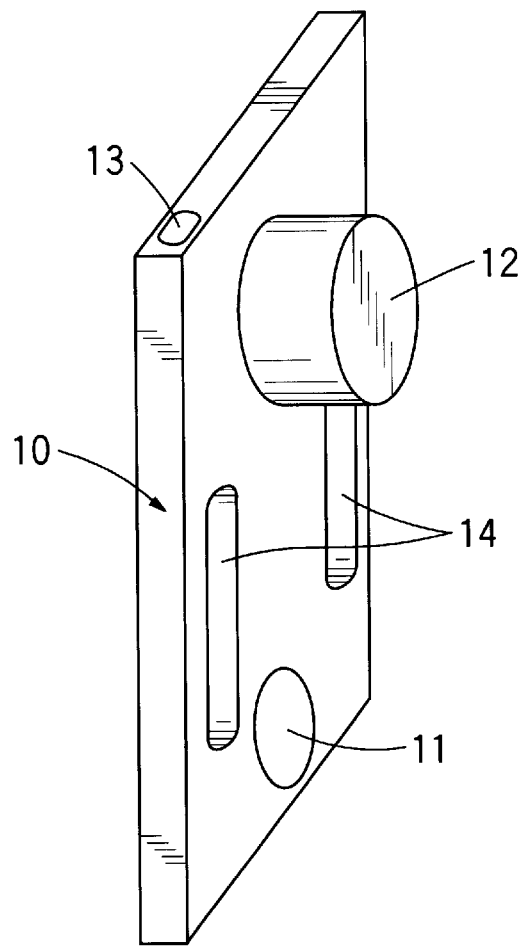
FIG. 3 is a perspective view of a first embodiment according to the present invention.
Figure 4:
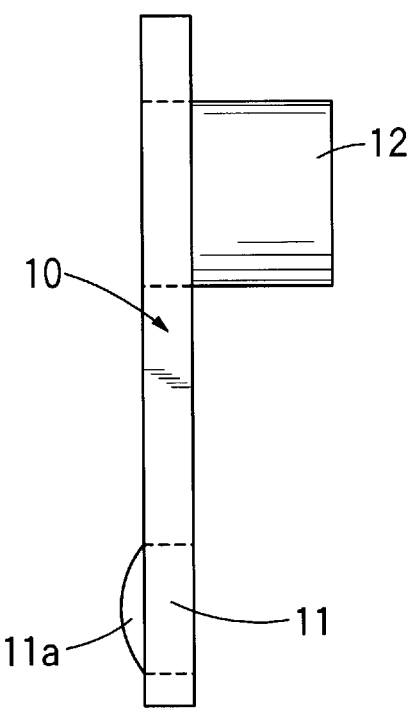
FIG. 4 is a side view of the first embodiment according to the present invention.

FIGS. 3 and 4 are perspective and side views each representing a subcutaneous fat measuring apparatus 10 according to a first embodiment of the present invention. The subcutaneous fat measuring apparatus 10 includes a reference position setting device 11 for positioning the apparatus 10 by setting a projection 11a at the reference point or the navel 7 of a person under test. An ultrasonic probe 12 including an ultrasonic transmitter and an ultrasonic receiver is mounted on the apparatus 10 at the position above the reference position setting device 11. The ultrasonic probe 12 may be any one of the commercially available devices, and therefore, there is no need for detailed description of the probe 12. The measuring apparatus 10 includes a measurement start switch 13 mounted on the upper side thereof. A person under test can operate the switch 13 by himself to start the measurement of subcutaneous fat thickness. The measuring apparatus 10 further includes belt holes 14 through which a belt is passed for fixing the apparatus 10 on the front side of the abdomen of the person.

Then an operation of the subcutaneous fat measuring apparatus 10 will be described. A belt (not shown) is inserted into one of the belt holes 14 and wrapped around the abdominal region of the person. Then the belt is inserted into another belt hole 14 and is fastened. Thereafter, the apparatus 10 is properly positioned by setting the projection 11a at the navel 7 of the person and aligning the apparatus 10 in parallel with the median line 2. Then the measurement start switch 13 is switched on to operate the apparatus 10. Now the ultrasonic probe 12 is positioned on the median line 2 and is ready for properly measuring the subcutaneous fat thickness.

Preferably, the interval between the projection 11a and the ultrasonic probe 12 is determined in such manner that the ultrasonic probe 12 is set at the position 2 cm above the navel 7 of the person along the median line 2. Alternatively the ultrasonic probe 12 may be slidably mounted on the apparatus 10 so that the probe 12 may be moved to any position on the median line 2.

The apparatus 10, of course, includes an additional control circuit for measurement, display means for displaying the result of measurement, and the like. If such control circuit and display means are incorporated into another separate device, they may be connected via cables, radio or optical communication means.

Figure 5:
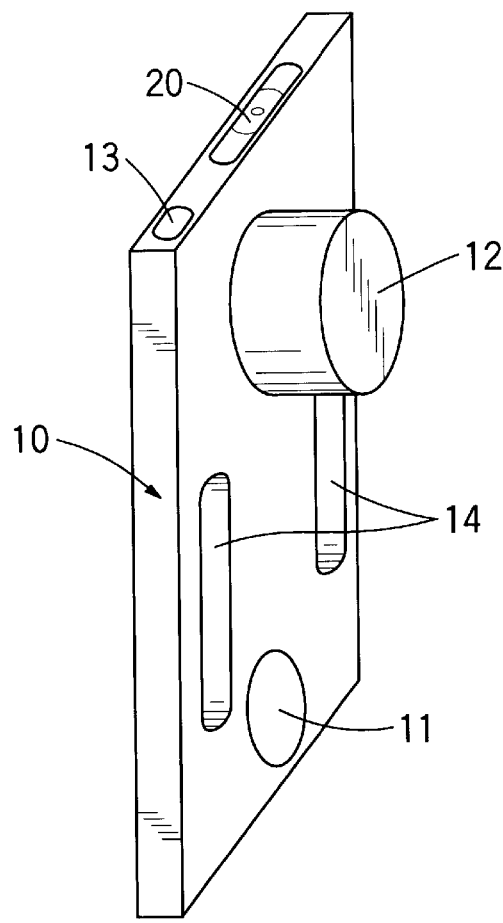
FIGS. 5, 6, 7, 8 and 9 represent modified forms of the first embodiment according to the present invention.

FIG. 5 represents a modified form of the first embodiment of the measuring apparatus 10. It includes basically the same components and functions as those in the first embodiment, as shown in FIGS. 3 and 4. In addition, the measuring apparatus 10 in FIG. 5 includes an additional component or a leveling instrument 20 that is mounted adjacent the measurement start switch 13 at the middle of upper surface of the apparatus 10. When the leveling instrument 20 indicates a horizontal position, it means that the apparatus 10 is positioned horizontal. In other words, the ultrasonic probe 12 becomes vertical to the reference position setting device 11 at the navel 7 of the person so that the probe 12 is properly positioned on the median line 2. Therefore, the person under test can easily perform the measurement of the subcutaneous fat on the median line 2.

Figure 6:
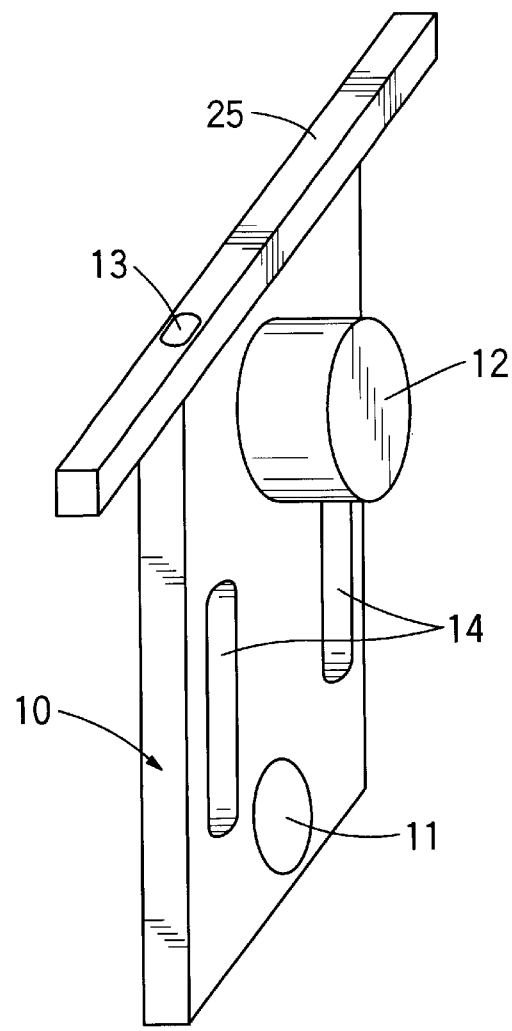

FIG. 6 represents another modified form of the measuring apparatus 10 in which the leveling instrument 20 in FIG. 5 is replaced with a lateral rod 25 that is mounted on the top portion of the apparatus 10. The lateral rod 25 is positioned horizontal by manual operation so that the ultrasonic probe 12 can be set on the median line 2 for easy and precise measurement of the subcutaneous fat, as in the case of the leveling instrument 20.

Figure 7:
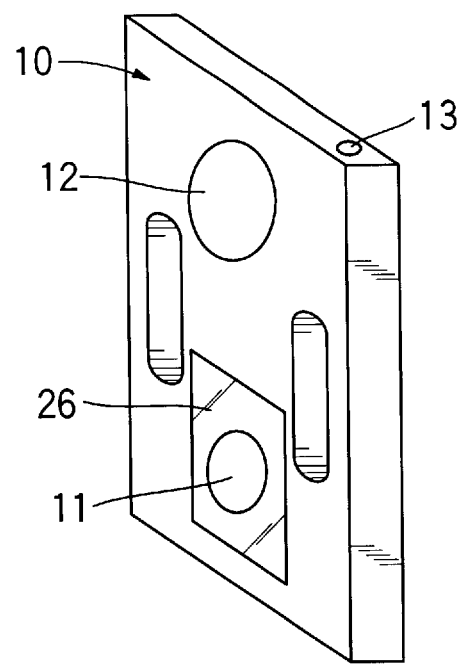

FIG. 7 represents a further modified form in which a positioning mirror 26 is mounted on the abdomen contact surface of the measuring apparatus 10. In operation, the person under test puts the lower portion of the measuring apparatus 10 on his abdomen and moves the apparatus 10 while watching the mirror 26 until the center of the mirror 26 is aligned with the navel 7 of the person. Then the person adjusts the position of the apparatus 10 so that the ultrasonic probe 12 is located over the median line 2 while keeping the apparatus 10 in horizontal position. Thereafter, he operates the switch 13. This form of the apparatus 10 provides for easy measurement of the subcutaneous fat in abdomen, as in the cases stated above.

Figure 8:
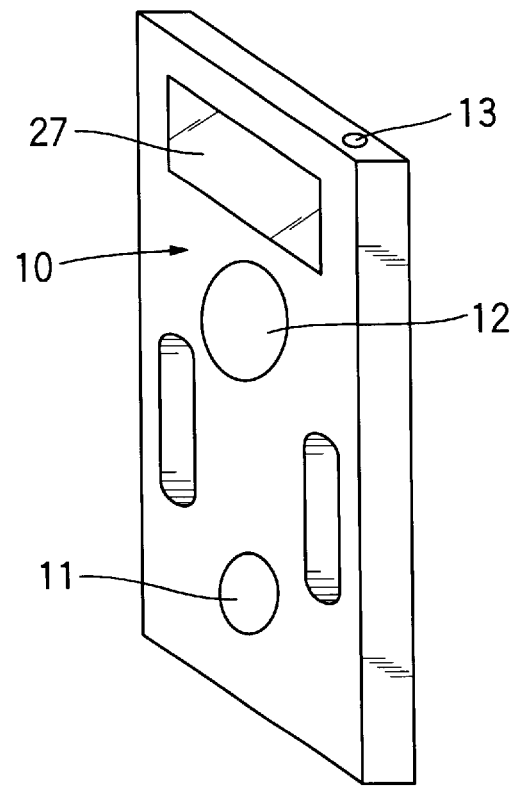

FIG. 8 represents a yet further modified form in which a display 27 is added to the measuring apparatus 10 in FIGS. 3 and 4 for displaying the result of measurement. After completion of the measurement, the person detaches the apparatus 10 from his abdomen to see the measurement result on the display 27.

Figure 9:
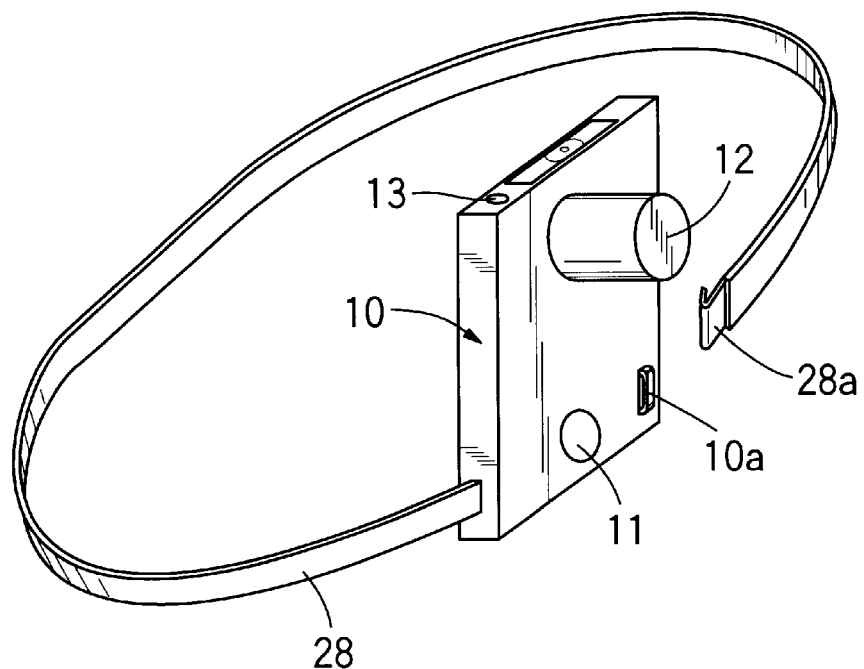

FIG. 9 represents a yet further modified form in which a device for measuring the girth of abdomen is added to the apparatus 10 in FIG. 5. More particularly the apparatus 10 includes a reel for winding a belt 28 and an instrument for measuring the length of the belt unwound. The person picks Up an end 28a of the belt 28, unwinds the belt 28, wraps it around the abdomen of the person, and fixes the belt end 28a to a hook 10a of the apparatus 10. Then the girth of abdomen is measured, together with the measurement of subcutaneous fat in abdomen, which enables easy estimation of the area of abdominal subcutaneous fat and the total amount of subcutaneous fat.

Figure 10:
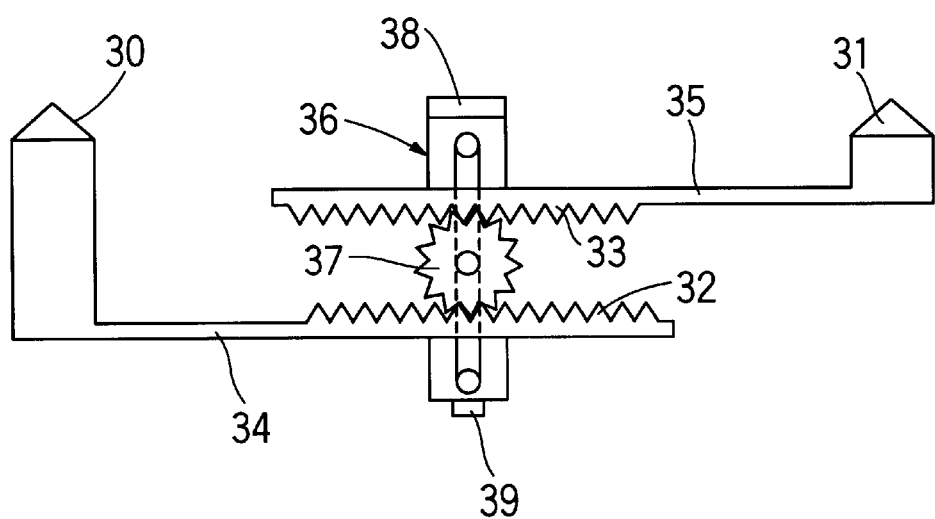
FIG. 10 is a front view of a second embodiment according to the present invention.

FIG. 10 represents a second embodiment of a measuring apparatus 36 for measuring the subcutaneous fat in an arm of the person according to the present invention. Reference numeral 30 represents a shoulder contact portion for making contact with a shoulder joint of the person, and 31 represents an elbow contact portion for making contact with an elbow joint of the person. The contact portions 30 and 31 are supported on support members 34 and 35 having rack portions 32 and 33 formed thereon, respectively. The support members 34 and 35 are movable to each other through a gear 37 sandwiched therebetween within the measuring apparatus 36. The measuring apparatus 36 includes an ultrasonic probe 38 at one side thereof and a measurement start switch 39 at the opposite side thereof. In operation of the apparatus 36, the shoulder contact portion 30 is put on the shoulder joint of the person and the elbow contact portion 31 is put on the elbow joint of the person while adjusting the interval between both contact portions. Thus the ultrasonic probe 38 can be positioned at mid point between the shoulder and the elbow of the person, irrespective of his arm length. Then the measurement start switch 39 is operated to measure the subcutaneous fat in the arm. If it is desired that the measurement of the subcutaneous fat is performed at the position apart from the mid point between the shoulder and the elbow by a predetermined distance, the ultrasonic probe 38 may be modified so that it is movable relative to the measuring apparatus 36 by means of an oval hole and the like.

The measuring apparatus 36 in FIG. 10 is generally adapted for measuring the subcutaneous fat in the arm of the person. But the apparatus can measure the subcutaneous fat in the flank by putting the shoulder contact portion 30 on the armpit and the elbow contact portion 31 on the hipbone of the person. In addition, the apparatus can measure the subcutaneous fat in a leg of the person by putting the contact portions 30, 31 on the knee and the heel, respectively. Furthermore, it can measure the subcutaneous fat in the back of the person by putting the contact portions 30, 31 on the shoulder and the shoulder blade region of the person, respectively.

The measuring apparatus 36 in FIG. 10 is designed to measure the subcutaneous fat by making contact with two specified measuring points on the person. However, depending on the place where there is no adverse effect produced to the measurement result, irrespective of some displacement of the measuring points, it may possible that only one of the measuring points is assigned, but another point is not specifically assigned.

Figure 11:
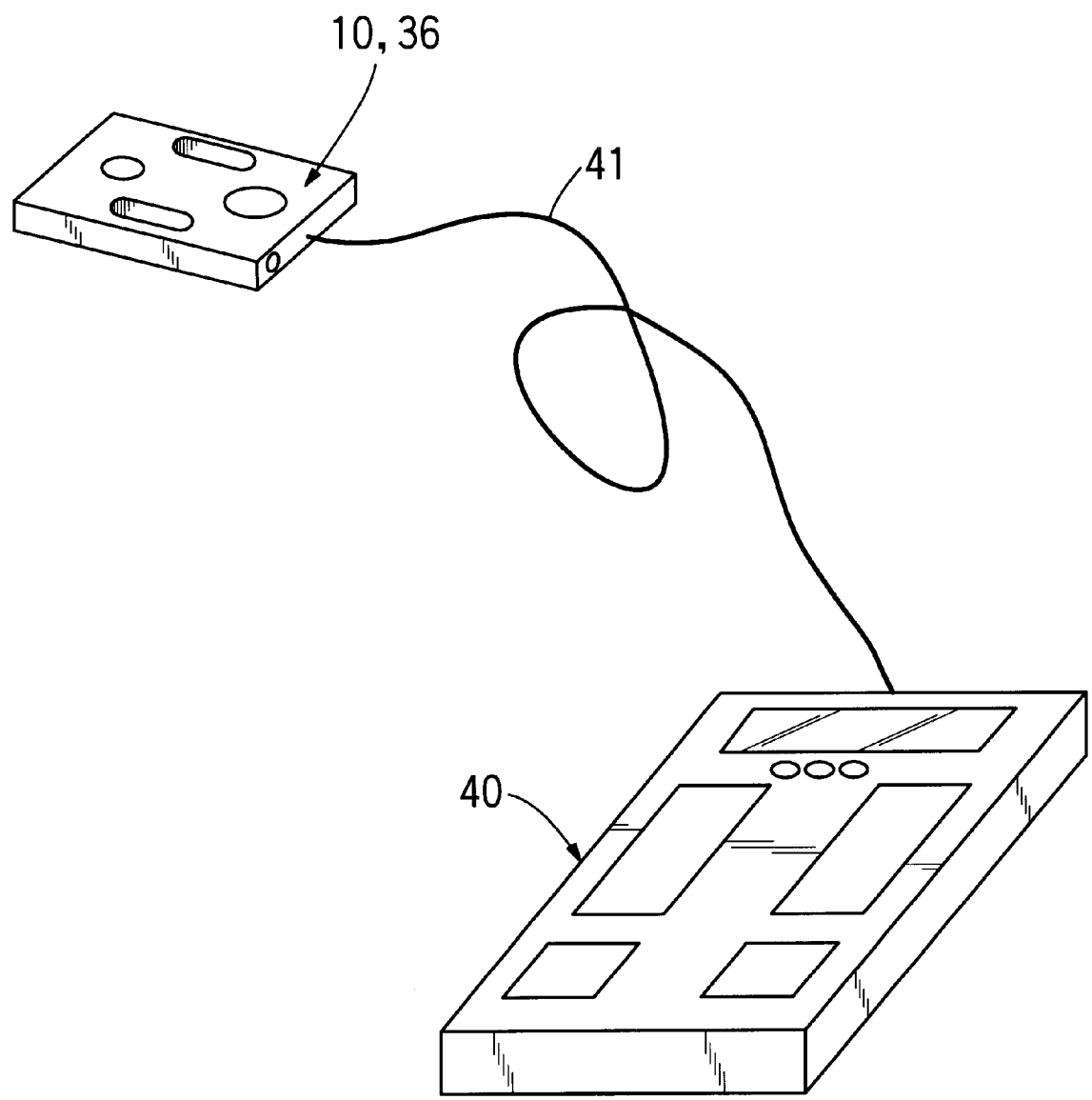
FIG. 11 represents a combination of the subcutaneous fat measuring apparatus according to the present invention with a body fat/weight measuring instrument.

The measuring apparatus of the present invention has been described above, as used for measuring the subcutaneous fat for the person. However, the measuring apparatus may also apply to other application, such as that shown in FIG. 11. In such case, the measuring apparatus of the present invention is used in combination with a body fat/weight measuring instrument 40 via a cable 41 or other wireless communication means such as a radio or an optical means. This allows the facilitated measurement of body fit percentage for a whole body, the amount of subcutaneous fat, and the area of subcutaneous fat.

In addition, the ultrasonic probe has been described above, as having an ultrasonic transmitter and an ultrasonic receiver. It is noted that when measuring in "A" mode of operation, one and the same device can be used for both transmitter and receiver.

It is apparent from the foregoing that a method for measuring subcutaneous fat using an ultrasonic wave has been provided according to the present invention in which it comprises a step of measuring a portion of an abdomen on a median line of a person under test. Therefore, the reliable measurement of the thickness of the subcutaneous fat 5 can be attained without any influence of the muscle 3.

The portion of the abdomen on the median line is between a sternum and a pubis of the person under test, and more preferably it is around 2 cm above a navel of the person under test. Therefore, the subcutaneous fat thickness measured can be used for estimating the area of abdominal subcutaneous fat and the total amount of subcutaneous fat.

Furthermore, an apparatus for measuring subcutaneous fat using an ultrasonic wave has been provided according to the present invention in which it comprises: a reference position setting device which sets the apparatus at a reference position on a person under test; an ultrasonic transmitter disposed at the predetermined position relative to the reference position setting device; and an ultrasonic receiver disposed at the predetermined position relative to the reference position setting device. Therefore, even unskilled persons can easily perform the precise measurement of subcutaneous fat with higher repeatability.

Because of the navel of the person defined as the reference point for measurement, the person under test can perform the measurement by himself.

Because of the ultrasonic transmitter and receiver positioned for measuring the subcutaneous fat in a position around 2 cm above the navel along the median line, there is no adverse effect of muscles in the abdominal region produced, and therefore, the reliable measurement of subcutaneous fat can be performed.

In addition, because of the shoulder joint defined as the reference point for measurement, the measurement of subcutaneous fat in an arm of the person can easily be performed without any positional displacement.

Furthermore, because of one and the same device used for both ultrasonic transmitter and receiver, the subcutaneous fat measuring apparatus can be manufactured with simplified construction.

What is claimed is:

1. A method for measuring subcutaneous fat using an ultrasonic wave, comprising the steps of:
   measuring a thickness of subcutaneous fat in a portion of an abdomen on a median line of a person under test; and
   calculating an area of the abdominal subcutaneous fat or a total amount of the subcutaneous fat on the basis of said measured thickness of the subcutaneous fat.

2. A method according to claim 1 in which said portion of the abdomen on the median line is between a sternum and a pubis of the person under test.

3. A method according to claim 2 in which said portion of the abdomen on the median line is about 2 cm above a navel of the person under test.

4. An apparatus for measuring subcutaneous fat using an ultrasonic wave, comprising:
   a reference position setting device which sets said apparatus at a reference position for measurement on a person under test;
   an ultrasonic transmitter disposed at a predetermined position relative to said reference position setting device;
   an ultrasonic receiver disposed at the predetermined position relative to said reference position setting device;
   a subcutaneous fat thickness measuring unit for measuring a thickness of subcutaneous fat on the basis of an output of said ultrasonic transmitter and said ultrasonic receiver; and
   a subcutaneous fat calculating unit for calculating an area of abdominal subcutaneous fat or a total amount of the subcutaneous fat on the basis of said measured thickness of subcutaneous fat.

5. An apparatus for measuring subcutaneous fat according to claim 4 in which a navel of the person is defined as the reference position for measurement.

6. An apparatus for measuring subcutaneous fat according to claim 4 in which said ultrasonic transmitter and said ultrasonic receiver are disposed for measuring the subcutaneous fat in an area about 2 cm above the navel of the person along a median line.

7. An apparatus for measuring subcutaneous fat according to claim 4 in which a shoulder joint of the person is defined as the reference position for measurement.

8. An apparatus for measuring subcutaneous fat according to claim 4 in which said ultrasonic transmitter and said ultrasonic receiver are formed by one and the same device.

9. An apparatus for measuring subcutaneous fat according to claim 4 in which it further comprises a measurement start switch, said measurement start switch being provided on the upper side of said apparatus.

10. An apparatus for measuring subcutaneous fat according to claim 4 further comprising a body fat/weight measuring instrument, and said subcutaneous fat calculating unit is for measuring the area of abdominal subcutaneous fat or the total amount of subcutaneous fat on the basis of said measured weight and said measured thickness of subcutaneous fat.

11. An apparatus for measuring subcutaneous fat according to claim 10, wherein said subcutaneous fat thickness measuring unit is connected to said body fat/weight measuring instrument via a cable or wireless communication means.

12. An apparatus for measuring subcutaneous fat according to claim 11, wherein the subcutaneous fat thickness measuring unit is connected to said body fat/weight measuring instrument via a radio.

13. An apparatus for measuring subcutaneous fat according to claim 11, wherein the subcutaneous fat thickness measuring unit is connected to said body fat/weight measuring instrument via optical means.

14. An apparatus for measuring subcutaneous fat according to claim 10 in which said ultrasonic transmitter and said ultrasonic receiver are disposed for measuring the subcutaneous fat in an area about 2 cm above the navel of the person along a median line.

15. An apparatus for measuring subcutaneous fat according to claim 10 in which a shoulder joint of the person is defined as the reference position for measurement.

16. An apparatus for measuring subcutaneous fat according to claim 10 in which said ultrasonic transmitter and said ultrasonic receiver are one and the same device.

17. An apparatus for measuring subcutaneous fat according to claim 10 in which it further comprises a measurement start switch on the upper side of said apparatus.

18. An apparatus for measuring subcutaneous fat according to claim 4 further comprising a girth measuring device for measuring the girth of an abdomen, and said subcutaneous fat calculating unit is for calculating the area of abdominal subcutaneous fat or the total amount of subcutaneous fat on the basis of said measured girth of the abdomen and said measured thickness of subcutaneous fat.

19. An apparatus for measuring subcutaneous fat according to claim 18 in which said ultrasonic transmitter and said ultrasonic receiver are disposed for measuring the subcutaneous fat in an area about 2 cm above the navel of the person along a median line.

20. An apparatus for measuring subcutaneous fat according to claim 18 in which a shoulder joint of the person is defined as the reference position for measurement.

21. An apparatus for measuring subcutaneous fat according to claim 18 in which said ultrasonic transmitter and said ultrasonic receiver are one and the same device.

22. An apparatus for measuring subcutaneous fat according to claim 18 in which it further comprises a measurement start switch on the upper side of said apparatus.

* * * * *